United States Patent [19]
Brown et al.

[11] Patent Number: 5,280,026
[45] Date of Patent: Jan. 18, 1994

[54] THIENOPYRIMIDINES

[75] Inventors: Thomas H. Brown; Robert J. Ife; Colin A. Leach, all of Welwyn, England

[73] Assignee: SmithKline Beecham Intercredit B.V., Rijswijk, Netherlands

[21] Appl. No.: 982,106

[22] Filed: Nov. 24, 1992

Related U.S. Application Data

[63] Continuation of Ser. No. 803,249, Dec. 5, 1991, abandoned, which is a continuation of Ser. No. 527,615, May 23, 1990, abandoned.

[51] Int. Cl.⁵ .................. C07D 495/04; C07D 333/38; A61K 31/505
[52] U.S. Cl. .................. 514/258; 544/278; 549/69; 549/70
[58] Field of Search .................. 514/258; 544/278

[56] References Cited

U.S. PATENT DOCUMENTS

| | | | |
|---|---|---|---|
| 3,931,204 | 1/1976 | Croisier | 544/279 |
| 4,146,716 | 3/1979 | Cox et al. | 544/278 |
| 4,196,207 | 4/1980 | Webber | 544/278 |
| 5,124,331 | 6/1992 | Arita | 544/278 |

FOREIGN PATENT DOCUMENTS 2200765 12/1973 Fed. Rep. of Germany.
1309182 7/1973 United Kingdom.

OTHER PUBLICATIONS

Robba, Bull. Chem. Soc. France, Pt 2, 592–597 (1975).

*Primary Examiner*—Mark L. Berch
*Attorney, Agent, or Firm*—Linda E. Hall; Stuart R. Suter; Edward T. Lentz

[57] ABSTRACT

Thienopyrimidine compounds are disclosed as inhibitors of the $H^+K^+$ATPase enzyme useful in the treatment of gastric acid secretion. A compound of the invention is 2-(2-methylphenylamino)-4-(N-methylphenylamino)thieno[3,2-d]pyrimidine.

14 Claims, No Drawings

THIENOPYRIMIDINES

This is a continuation of application Ser. No. 07/803,249, filed Dec. 5, 1991, abandoned, which is a continuation of application Ser. No. 07/527,615 filed May 23, 1990, abandoned.

COMPOUNDS

The present invention relates to substituted thienopyrimidine derivatives, processes for their preparation, intermediates useful in their preparation, pharmaceutical compositions containing them and their use in therapy.

Accordingly the present invention provides, in a first aspect compounds of structure (I)

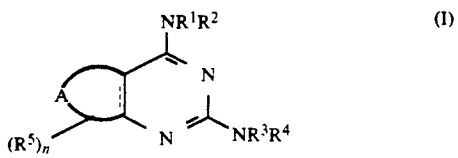

in which $R^1$ and $R^2$ are the same, or different and are each hydrogen, $C_{1-4}$alkyl, -$(CH_2)_nAr$ in which n is 0 to 4 and Ar is an optionally substituted phenyl group, or $R^1$ and $R^2$ together with the nitrogen atom to which they are attached form a saturated or unsaturated ring optionally containing one or more further heteroatoms; and;

$R^3$ and $R^4$ are the same or different and are each hydrogen, $C_{1-4}$alkyl, $(CH_2)_nAr^1$ in which n is 0 to 4 and $Ar^1$ is an optionally substituted phenyl group, or $R^3$ and $R^4$ together with the nitrogen atom to which they are attached form a saturated or unsaturated ring optionally containing one or more further heteroatoms.

$R^5$ is hydrogen, $C_{1-4}$alkyl, $C_{1-4}$alkoxy or $COC_{1-4}$alkyl;

n is 1 or 2;

A is —SCH=CH—, —CH=CHS— or =CHSCH=, and the dotted line indicates the presence of a double bond when A is —SCH=CH— or —CH=CHS—;

and pharmaceutically acceptable salts thereof.

Suitably $R^1$ and $R^2$ are the same or different and are each hydrogen or $(CH_2)_nAr$ in which n is 0 to 4 and Ar is an optionally substituted phenyl group or $R^1$ and $R^2$ together with the nitrogen atom to which they are attached form a saturated or unsaturated ring optionally containing one or more further heteroatoms. More suitably, one of $R^1$ and $R^2$ is hydrogen or $C_{1-4}$alkyl and the other is hydrogen, $C_{1-4}$alkyl or $(CH_2)_nAr$. Most suitably one of $R^1$ and $R^2$ is hydrogen or $C_{1-4}$alkyl and the other is $(CH_2)_nAr$. Preferably one of $R^1$ and $R^2$ is $C_{1-4}$alkyl and the other is $(CH_2)_nAr$; most preferably one of $R^1$ and $R^2$ is $C_{1-4}$alkyl, in particular methyl and the other is $(CH_2)_nAr$ in which n is 0.

Suitably, Ar is unsubstituted or substituted by 1 to 3 substituents selected from hydrogen, $C_{1-4}$alkyl, $C_{1-4}$alkoxy, $C_{1-4}$alkylthio, halogen, cyano, amino, hydroxy, carbamoyl, carboxy, $C_{1-4}$alkanoyl or trifluoromethyl. More suitably, Ar is unsubstituted or substituted by two substituents selected from hydrogen, $C_{1-4}$alkyl, $C_{1-4}$alkoxy, $C_{1-4}$alkylthio, halogen, cyano, amino, hydroxy, carbamoyl, carboxy, $C_{1-4}$alkanoyl or trifluoromethyl. More preferably, Ar is unsubstituted or substituted by two substituents selected from $C_{1-4}$alkyl and $C_{1-4}$alkoxy. Most preferably, Ar is unsubstituted or substituted by a single substituent selected from the above-noted groups, in particular $C_{1-4}$alkyl or $C_{1-4}$alkoxy.

Suitably, $R^3$ and $R^4$ are the same or different and are each hydrogen, $C_{1-4}$alkyl, $(CH_2)_nAr^1$ in which n is 0 to 4 and $Ar^1$ is an optionally substituted phenyl group, or $R^3$ and $R^4$ together with the nitrogen atom to which they are attached form a saturated or unsaturated ring optionally containing one or more further heteroatoms. More suitably one of $R^3$ and $R^4$ is hydrogen or $C_{1-4}$alkyl and the other is hydrogen, $C_{1-4}$alkyl or $(CH_2)_nAr^1$, or $R^3$ and $R^4$ together with the nitrogen atom to which they are attached form a saturated or unsaturated carbocyclic ring. Most suitably, one of $R^3$ and $R^4$ is hydrogen or $C_{1-4}$alkyl and the other is hydrogen, $C_{1-4}$alkyl or $(CH_2)_nAr^1$. Preferably one of $R^3$ and $R^4$ is hydrogen or $C_{1-4}$alkyl and the other is $(CH_2)_nAr^1$; more preferably one of $R^3$ and $R^4$ is hydrogen and the other is $(CH_2)_nAr^1$; most preferably, one of $R^3$ and $R^4$ is hydrogen and the other is $(CH_2)_nAr^1$ in which n is O.

Suitably, the group $Ar^1$ is unsubstituted or optionally substituted by 1 to 3 substituents as hereinabove described for the group Ar in $R^1$ or $R^2$. Preferably the group $Ar^1$ is substituted by one or two groups, for example a $C_{1-4}$alkyl group, in particular a methyl group or a halogen atom, in particular a fluorine atom; or a $C_{1-4}$alkyl group and a halogen atom or $C_{1-4}$alkoxy group in particular a methyl group and fluorine atom or methoxy group and fluorine atom. More preferably the group $Ar^1$ is substituted by a single group in the 2-position of the ring in particular, a methyl group.

Suitably $R^5$ is hydrogen, $C_{1-4}$alkyl, $C_{1-4}$alkoxy or $COC_{1-4}$alkyl; preferably $R^5$ is hydrogen.

Suitably n is 1 or 2; preferably n is 1.

Suitably, A is =CHSCH=, —CH=CHS— or —SCH=CH—; preferably A is —SCH=CH—.

$C_{1-4}$alkyl groups (either alone or as part of another group) can be straight or branched.

It will be appreciated that compounds of structure (I) in which one or more of $R^1$ to $R^5$ is a $C_{3-4}$alkyl group (either alone or as part of another group) may contain an assymetric centre due to the presence of the $C_{3-4}$alkyl group. Such compounds will exist as two (or more) optical isomers (enantiomers). Both the pure enantiomers, racemic mixtures (50% of each enantiomer) and unequal mixtures of the two are included within the scope of the present invention. Further, all diastereomeric forms possible (pure enantiomers and mixtures thereof) are within the scope of the invention.

The compounds of the present invention can be prepared by processes analogous to those known in the art for example by:

(a) reaction of a compound of structure (II)

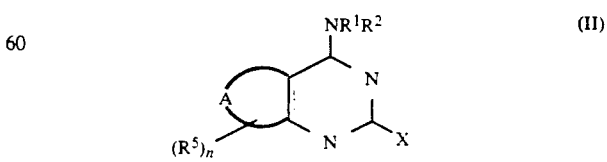

in which $R^1$, $R^2$, $R^5$, A and n are as described for structure (I) except that where necessary they are in protected form, and X is a group displaceable by an amine, with an amine of structure $R^3R^4NH$ in which $R^3$ and $R^4$ are as described for structure (I);

(b) reaction of a compound of structure (III)

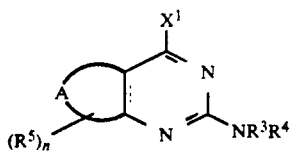
(III)

in which $R^3$, $R^4$, $R^5$, A and n are as described for structure (I) and $X^1$ is a group displaceable by an amine, with an amine of structure $R^1R^2NH$ in which $R^1$ and $R^2$ are as described for structure (I); or (c) for compounds of structure (I) in which $NR^1R^2$ and $NR^3R^4$ are the same, reaction of a compound of structure (IV)

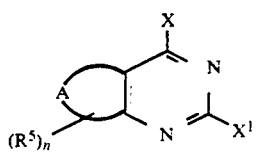
(IV)

in which A, $R^5$ and n are as described for structure (I) and X and $X^1$ are groups displaceable by an amine, with an amine of structure $R^1R^2NH$ or $R^3R^4NH$ and optionally thereafter, removing any protecting groups;
forming a pharmaceutically acceptable salt.

Suitable groups displaceable by an amine, X and $X^1$, will be apparent to those skilled in the art and include, for example, halogen, in particular chlorine, $SC_{1-4}$alkyl, such as methylthio, hydroxy and phenoxy.

Reaction of a compound of structure (II) with an amine $R^3R^4NH$ is suitably carried out in an inert solvent at elevated temperature. Preferably the reaction is carried out in the absence of a solvent at elevated temperature.

Reaction of a compound of structure (III) with an amine $R^1R^2NH$ is suitably carried out in the presence or absence of an inert solvent, preferably in the absence of a solvent.

Reaction of a compound of structure (IV) with a suitable amine is suitably carried out under similar conditions to those described for the reaction of a compound of structure (III) and an amine of structure $R^1R^2NH$.

In particular, leaving groups X and $X^1$ are halogen, preferably chlorine, and can be displaced by appropriate amines $R^1R^2NH$ and $R^3R^4NH$ under the general conditions described above and in the specific examples. Other conditions and reagents depending on the nature of the leaving groups will be apparent to those skilled in the art; for example compounds of structure (I) in which $R^1$ and $R^2$ are both hydrogen, can be prepared from the corresponding compounds of structure (III) in which X is hydroxy by reaction with phenylphosphordiamidate using the method described in J. Het. Chem (1972), 9, 1235.

Pharmaceutically acceptable acid addition salts of the compounds of structure (I) can be prepared by standard procedures by, for example, reaction with suitable organic and inorganic acids the nature of which will be apparent to persons skilled in the art. For example, pharmaceutically acceptable salts can be formed by reaction with hydrochloric, sulphuric, or phosphoric acids; aliphatic, aromatic or heterocyclic sulphonic acids or carboxylic acids such as, for example, citric, maleic or fumaric acids.

The intermediate compounds of structure (II) and (III) can be prepared by procedures analogous to those known in the art. The amines of structure $R^1R^2NH$ and $R^3R^4NH$ are available commercially or can be prepared by standard techniques well known to those skilled in the art of organic chemistry.

For example compounds of structure (II) in which A is $-CH=CHS-$ or $-SCH=CH-$ and X is chlorine can be prepared by the route outlined in Scheme I.

Scheme I

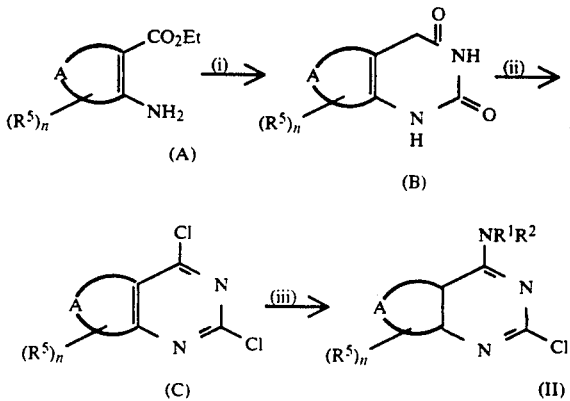

(i) Urea
(ii) $POCl_3$, $PhNMe_2$, $\Delta$
(iii) $R^1R^2NH$, EtOH.

Compounds of structure (III) in which A is $-SCH=CH-$ and X is chlorine can be prepared by the procedures outlined in Scheme II.

Scheme II

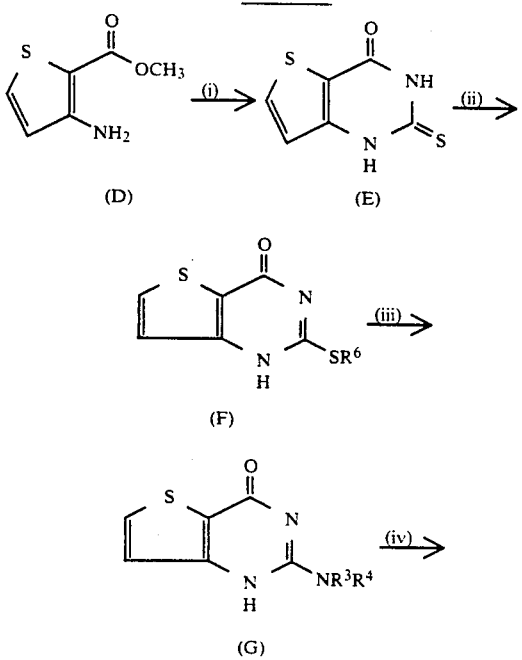

-continued
Scheme II

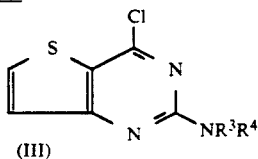

(i) KSCN, HCl
(ii) $R^6X^2$, NaOH ($R^6 = C_{1-4}$alkyl, $X^2$ = halogen)
(iii) $R^3R^4NH$,
(iv) $POCl_3$, $\Delta$ Compounds of structure (III) in which A is =CH—SCH= can be prepared via the reactions outlined in Scheme III below Scheme III

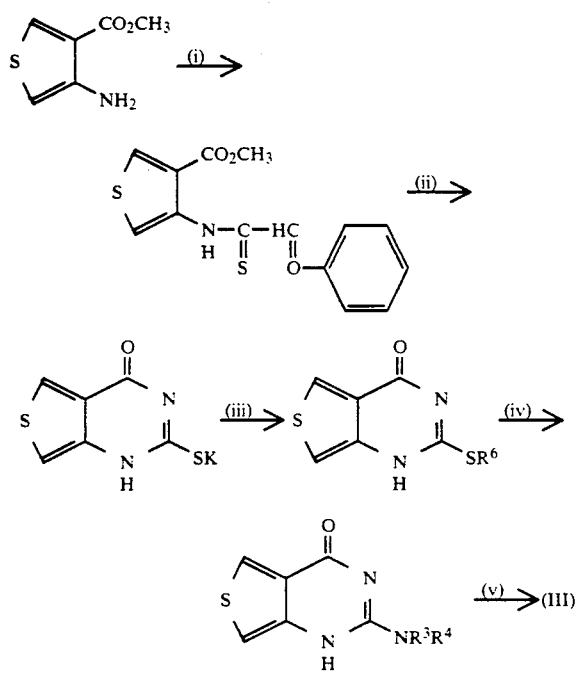

(i) benzoyl isothiocyanate, toluene
(ii) KOH, MeOH
(iii) $R^6X^2$ ($R^6 = C_{1-4}$alkyl, $X^2$ = halogen)
(iv) $HNR^3R^4$.
(v) $POCl_3\Delta$ The starting materials used to prepare compounds of structures (II) and (III) are available commercially or can be prepared by standard techniques.

In particular compounds (C) in Scheme I in which A is —CH=CHS— and $R^5$ is hydrogen are described in GB 1,570,494 and Bull Soc. Chim. France 529, 1975; compounds (C) in which A is SCH=CH and $R^5$ is hydrogen are described in DE 2,058,086; and compounds (F) from Scheme II in which $R^6$ is ethyl are disclosed in GB 1,309,182.

It is to be noted, and apparent to those skilled in the art that in the foregoing reactions, where necessary groups on aromatic rings Ar and $Ar^1$ (e.g. hydroxy or amino groups) will be in "protected" form. For example, amino groups can be "protected" in the form of nitro groups and converted into amino groups as appropriate, and hydroxy groups can be protected using standard groups for example as described in "Greene, T. W., Protective Groups in Organic Chemistry" which also provides examples of further appropriate protective groups for other moieties.

The compounds of structure (I) and their pharmaceutically acceptable salts exert an anti-secretory effect by inhibition of the gastrointestinal $H^+K^+$ATPase enzyme (Fellenius E., Berglindh T., Sachs G., Olke L., Elander B., Sjostrand S. E., and Wallmark B., 1981, Nature, 290, 159-61).

In a further aspect therefore the present invention provides compounds of structure (I) and pharmaceutically acceptable salts thereof for use in the treatment of gastrointestinal diseases in mammals, in particular humans. Such diseases include, for example, gastric and duodenal ulcers, and Zollinger-Ellison Syndrome. Further, the compounds of structure (I) can be used in the treatment of other disorders where an anti-secretory effect is desirable for example in patients with gastritis, NSAID induced gastritis, gastric ulcers, acute upper intestinal bleeding, in patients with a history of chronic and excessive alcohol consumption, and in patients with gastro oesophageal reflux disease (GERD).

In addition to the foregoing use the compounds of structure (I) can be of use in medicine as inhibitors of bone resorption. In normal subjects there is a balance between bone resorption and bone formation, however in subjects with bone affected diseases such as osteoporosis, Paget's disease and hyperparathyroidism and related disorders this balance is disturbed. As a consequence the subject suffers a loss of bone tissue, decreased bone mass and bone fragility which can result in fracturing of bones. Bone resorption (or bone loss) is associated with the activity of osteoclast cells and it is thought that agents which inhibit the activity of such cells (and so inhibit bone resorption) will have a beneficial effect on the reduction of bone loss and be of benefit in the treatment of the above-noted disease states. The present compounds can be expected to be inhibitors of osteoclast activity and bone resorption and to be of use in medicine in the treatment of diseases in which bone loss is a factor, in particular osteoporosis, Paget's disease and hyperparathyroidism.

In therapeutic use, the compounds of the present invention are usually administered in a standard pharmaceutical composition. The present invention therefore provides in a further aspect pharmaceutical compositions comprising a compound of structure (I) or a pharmaceutically acceptable salt thereof and a pharmaceutically acceptable carrier.

The compounds of structure (I) and their pharmaceutically acceptable salts which are active when given orally can be formulated as liquids, for example syrups, suspensions or emulsions, tablets, capsules and lozenges.

A liquid formulation will generally consist of a suspension or solution of the compound or pharmaceutically acceptable salt in a suitable liquid carrier(s) for example, ethanol, glycerine, non-aqueous solvent, for example polyethylene glycol, oils, or water with a suspending agent, preservative, flavouring or colouring agent.

A composition in the form of a tablet can be prepared using any suitable pharmaceutical carrier(s) routinely used for preparing solid formulations. Examples of such carriers include magnesium stearate, starch, lactose, sucrose and cellulose.

A composition in the form of a capsule can be prepared using routine encapsulation procedures. For example, pellets containing the active ingredient can be prepared using standard carriers and then filled into a hard gelatin capsule; alternatively, a dispersion or suspension can be prepared using any suitable pharmaceutical carrier(s), for example aqueous gums, celluloses, silicates or oils and the dispersion or suspension then filled into a soft gelatin capsule.

Typical parenteral compositions consist of a solution or suspension of the compound or pharmaceutically acceptable salt in a sterile aqueous carrier or parenterally acceptable oil, for example polyethylene glycol, polyvinyl pyrrolidone, lecithin, arachis oil or sesame oil. Alternatively, the solution can be lyophilised and then reconstituted with a suitable solvent just prior to administration.

A typical suppository formulation comprises a compound of formula (I) or a pharmaceutically acceptable salt thereof which is active when administered in this way, with a binding and/or lubricating agent such as polymeric glycols, gelatins or cocoa butter or other low melting vegetable or synthetic waxes or fats.

Preferably the composition is in unit dose form such as a tablet or capsule.

Each dosage unit for oral administration contains preferably from 1 to 250 mg (and for parenteral administration contains preferably from 0.1 to 25 mg) of a compound of the formula (I) or a pharmaceutically acceptable salt thereof calculated as the free base.

The present invention also provides a method of inhibiting gastric acid secretion which comprises administering to a mammal in need thereof an effective amount of a compound of structure (I) or a pharmaceutically acceptable salt thereof; and a method of treatment of diseases of the stomach or intestine based on increased acid secretion which comprises administering to a mammal in need thereof an effective amount of a compound of structure (I) or a pharmaceutically acceptable salt thereof.

The pharmaceutically acceptable compounds of the invention will normally be administered to a subject for the treatment of gastrointestinal diseases and other conditions caused or exacerbated by gastric acidity. The daily dosage regimen for an adult patient may be, for example, an oral dose of between 1 mg and 500 mg, preferably between 1 mg and 250 mg, or an intravenous, subcutaneous, or intramuscular dose of between 0.1 mg and 100 mg, preferably between 0.1 mg and 25 mg, of the compound of the formula (I) or a pharmaceutically acceptable salt thereof calculated as the free base, the compound being administered 1 to 4 times per day. Suitably the compounds will be administered for a period of continuous therapy, for example for a week or more.

In addition, the compounds of the present invention can be co-administered with further active ingredients, such as antacids (for example magnesium carbonate or hydroxide and aluminium hydroxide), non-steroidal anti-flammatory drugs (for example indomethacin, aspirin or naproxen), steroids, or nitrite scavengers (for example ascorbic acid or aminosulphonic acid), or other drugs used for treating gastric ulcers (for example pirenzipine, prostanoids for example 16,16 dimethyl PGE$_2$, or histamine H$_2$-antagonists (for example, cimetidine).

The following examples illustrate the invention. Temperatures are recorded in degrees centigrade.

THIENO[3,2-d]-PYRIMIDINES (a) 2-(2-Methylphenylamino)-4-hydroxythieno[3,2-d]-pyrimidine 2-Ethylmercapto-4-hydroxythieno[3,2-d]pyrimidine 10 g, 0.0471 mol) and o-toluidine (30 g, 0.0279 mol) were heated in an oil bath at 210° for 20 hours. The reaction mixture was poured into diethyl ether and the solid obtained was collected by filtration and dried. The mother liquor was extracted with 2N sodium hydroxide (3×100 ml). The aqueous extracts were combined, acidified with glacial acetic acid and extracted with chloroform (3×100 ml). The chloroform extracts were combined, dried over magnesium sulphate, filtered and evaporated under reduced pressure to give a solid. Recrystallization from methanol gave a pure sample, (5.32 g), m.p. 243°–245°.

Found C 60.82, H 4.36, N 16.64, S 12.02%;
Requires C 60.68, H 4.31, N 16.33, S 12.46%.

The following compounds were made in a similar manner.

2-(4-Methoxy-2-methylphenylamino)-4-hydroxythieno[3,2-d]-pyrimidine
m.p. 246°–248° (methanol).
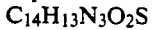
Found C 58.46, H 4.54, N 14.52, S 11.46%;
Requires C 58.52, H 4.56, N 14.62, S 11.16%.

2-(4-Fluoro-2-methylphenylamino)-4-hydroxythieno[3,2-d]-pyrimidine
m.p. 250°–252° (methanol).

(b) 2-(2-methylphenylamino)-4-chlorothieno[3,2-d]-pyrimidine 2-(2-Methylphenylamino)-4-hydroxythieno[3,2-d]-pyrimidine (2 g, 0.0078 mol) and phosphorus oxychloride (20 ml) were heated under reflux for 1 hour. The solution was poured onto ice, basified with concentrated NH$_3$ solution, and extracted with dichloromethane (3×100 ml). The dichloromethane extracts were combined, dried over magnesium sulphate and evaporated to give a yellow solid, 2.08 g. Recrystallization from methanol gave an analytically pure sample, m.p. 87°–89°.

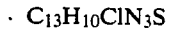
Found C 56.46, H 3.62, N 15.20, Cl 12.77, S 12.02%;
Requires C 56.62, H 3.66, N 15.24, Cl 12.86, S 11.63%.

The following compounds were prepared in a similar manner.

2-(4-Methoxy-2-methylphenylamino)-4-chlorothieno[3,2-d]-pyrimidine
m.p. 151°–153° (methanol)
Found C 54.82, H 4.13, N 13.68, Cl 11.23, S 10.65%;
Requires C 54.99, H 3.96, N 13.74, Cl 11.59, S 10.49%. 2-(4-Fluoro-2-methylphenylamino)-4-chlorothieno[3,2-d]-pyrimidine
m.p. 162°–164° (methanol)
Found C 52.92, H 3.33, N 14.09, Cl 12.08, S 10.97%;
Requires C 53.15, H 3.09, N 14.31, Cl 12.07, S 10.92%.

EXAMPLE 1

2-(2-Methylphenylamino)-4-(N-methylphenylamino)-thieno[3.2-d]pyrimidine.

2-(2-Methylphenylamino)-4-chlorothieno[3,2-d]-pyrimidine (1.5 g, 0.0054 mol) and N-methylaniline (1.16 g, 0.0054 mol) were heated in an oil bath at 140° for 2 hours. The reaction mixture was diluted with dichloromethane (100 ml) and washed with 2N hydrochloric acid (3×100 ml), then sodium carbonate solution. The dichloromethane extracts were dried over magnesium sulphate, filtered and evaporated to give a solid. Recrystallization from methanol gave the title compound, (0.75 g) m.p. 198°-200°.

C₂₀H₁₈N₄S
Found C 69.37, H 5.38, N 16.17, S 9.15%;
Requires C 69.34, H 5.24, N 16.17, S 9.26%.

EXAMPLE 2

2-(4-Methoxy-2-methylphenylamino)-4-(N-methylphenylamino)thieno[3,2-d]pyrimidine hydrochloride.

2-(4-Methoxy-2-methylphenylamino)-4-chlorothieno[3,2-d]pyrimidine (4 g, 0.013 mol) and N-methylaniline (2.8 g, 0.026 mol) were heated at 140° for 1 hour. The addition of diethyl ether gave a solid which was collected by filtration and dried, (5.5 g). Recrystallization from ethanol/diethyl ether gave the title compound, (4.59 g), m.p. 225°-227°.

C₂₁H₂₀N₄OS HCl
Found C 61.05, H 5.25, N 13.66, Cl⁻8.53, S 7.72%;
Requires C 61.08, H 5.13, N 13.57, Cl⁻8.59, S 7.77%.

EXAMPLE 3

2-(4-Fluoro-2-methylphenylamino)-4-(N-methylphenylamino)thieno[3,2-d]pyrimidine hydrochloride 2-(4-Fluoro-2-methylphenylamino)-4-chlorothieno-[3,2-d]pyrimidine (1.5 g, 0.0051 mol) and N-methylaniline were heated in an oil bath at 150° for 1 hour. Addition of diethyl ether gave a solid which was collected by filtration and dried, (1.85 g). Recrystallization from ethanol gave the title compound, (0.75 g), m.p. 242°-244°.

C₂₀H₁₇FN₄S HCl
Found C 60.18, H 4.35, N 14.14, Cl⁻8.64, S 8.19%;
Requires C 59.92, H 4.53, N 13.98, Cl⁻8.84, S 8.00%.

EXAMPLE 4

2,4-Bis(N-methylphenylamino)thieno[3,2-d]pyrimidine 2,4-Dichlorothieno[3,2-d]pyrimidine (1 g, 0.0048 mol) and N-methylaniline (5 ml) were heated at 130° for 1 hour. The reaction mixture was diluted with dichloromethane (200 ml) and extracted with 2N hydrochloric acid (3×150 ml). The organic phase was then washed with sodium carbonate, dried over magnesium sulphate, filtered and evaporated under reduced pressure to give a brown solid. Recrystallization from methanol gave the title compound, (1.08 g), m.p. 120°-122°.

C₂₀H₁₈N₄S
Found C 69.51, H 5.02, N 16.21, S 9.32%;
Requires C 69.34, H 5.24, N 16.17, S 9.26%.

THIENO[2,3-d]-PYRIMIDINES (a) 2-Chloro-4-(N-methylphenylamino)thieno[2,3-d]pyrimidine 2,4-Dichlorothieno[2,3-d]pyrimidine (4.5 g, 0.022 mol) and N-methylaniline (4.7 g, 0.044 mol) in ethanol (50 ml) were stirred at room temperature for 72 hours. The solid obtained was collected by filtration, washed with ethanol and dried, 5.15 g. Recrystallization from ethyl acetate gave the title compound, m.p. 167°-168°.

C₁₃H₁₀ClN₃S
Found C 56.72, H 3.75, N 15.25, Cl 12.99, S 11.84%;
Requires C 56.62, H 3.66, N 15.24, Cl 12.86, S 11.63%.

(b) 2-Chloro-4-(phenylamino)thieno[2,3-d]pyrimidine 2,4-Dichlorothieno[2,3-d]pyrimidine (3.2 g, 0.0156 mol) and aniline (2.9 g, 0.0311 mol) in ethanol were stirred at room temperature for 20 hours. The solvent was evaporated under reduced pressure to give an oil. The oil was treated with diethyl ether to give a solid, aniline hydrochloride. The filtrate was evaporated under reduced pressure to give the product as a solid, (3.74 g). Recrystallization (0.7 g) from methanol gave a pure sample of the title compound, (0.53 g), m.p. 149°-151°.

EXAMPLE 5

2-(2-Methylphenylamino)-4-(N-methylphenylamino)-thieno[2,3-d]pyrimidine hydrochloride.

2-Chloro-4-(N-methylphenylamino)thieno[2,3-d]pyrimidine (1.5 g, 0.0054 mol) and o-toluidine (1.3 g, 0.012 mol) were heated at 160° in an oil bath for 2 hours. The addition of methanol gave a solid which was collected by filtration and dried. Recrystallization from ethanolic HCl gave the title compound as a partial hydrochloride salt, (1.13 g), m.p. 210°-212°.

C₂₀H₁₈N₄S 0.65 HCl
Found C 64.92, H 5.17, N 15.04, S 8.47, Cl⁻6.51%;
Requires C 64.89, H 5.08, N 15.14, S 8.66, Cl⁻6.23%.

EXAMPLE 6

2-(4-Fluoro-2-methylphenylamino)-4-(N-methylphenylamino)thieno-[2,3-d]pyrimidine hydrochloride 2-Chloro-4-(N-methylphenylamino)thieno[2,3-d]-pyrimidine (1.5 g, 0.00544 mol) and 4-fluoro-2-methylphenylamine (1.5 g, 0.0120 mol) were heated at 160° for 2.5 hours. Addition of methanol gave a solid which was collected by filtration and dried, (1.81 g). Recrystallization from ethanolic HCl/methanol gave the title compound as the hydrochloride salt, (1.44 g), m.p.216°-218°.

C₂₀H₁₇FN₄S HCl
Found C 59.96, H 4.54, N 13.85, S 8.19, Cl⁻8.69%;
Requires C 59.92, H 4.53, N 13.98, S 8.00, Cl⁻8.64%.

EXAMPLE 7

2-(2-Methylphenylamino)-4-(phenylamino)thieno[2,3-d]-pyrimidine hydrochloride

2-Chloro-4-(phenylamino)thieno[2,3-d]pyrimidine (3 g, 0.0115 mol) and o-toluidine (2.46 g, 0.023 mol) were heated at 140° for 3 hours. Addition of diethyl ether gave a solid which was collected by filtration and dried, (3.7 g). Recrystallization from ethanolic HCl gave the title compound as the hydrochloride salt, (1.67 g), m.p. 232°-234°.

C₁₉H₁₆N₄S, HCl
Found C 61.51, M 4.72, N 14.88, S 6.67, Cl⁻9.51;
Requires C 61.86, M 4.65, N 15.19, S 8.69, Cl⁻9.61.

EXAMPLE 8

2,4-Bis(N-methylphenylamino)thieno(2,3-d)pyrimidine 2,4-Dichlorothieno[2,3-d]pyrimidine (2 g, 0.00975 mol) and N-methylaniline (5 ml) were heated in an oil bath at 150° for 2 hours. The reaction mixture was dissolved in chloroform (200 ml) and extracted with 2N hydrochloric acid (3×100 ml). The chloroform solution was then washed with sodium carbonate solution, dried over magnesium sulphate, filtered and evaporated to give an oil. The oil was purified by chromatography using dichloromethane as eluant. The solid obtained was recrystallized from ether/petroleum ether (b.p. 40°-60°) to give the title compound, (1.2 g) m.p. 85°-87°.

C₂₀H₁₈N₄S
Found C 68.96, H 5.36, N 16.06, S 9.14%;
Requires C 69.34, H 5.24, N 16.17, S 9.26%.

EXAMPLE 9

2,4-(2-methylphenylamino)thieno[2,3-d]pyrimidine

2,4-Dichlorothieno[2,3-d]pyrimidine (1.5 g, 0.0073 mol) and o-toluidine (5 ml) were heated in an oil bath at 160° for 2 hours. The reaction mixture was dissolved in chloroform (200 ml) and washed with 2N hydrochloric acid (3×100 ml), then sodium carbonate solution, dried over magnesium sulphate, filtered and evaporated under reduced pressure to give a solid, (1.98 g). The solid was purified by column chromatography using dichloromethane as eluant. The fractions containing the product were combined and evaporated under reduced pressure to give a solid. Recrystallization from diethyl ether/petroleum ether (b.p. 40°-60°) gave the title compound, (1.0 g), m.p. 121°-123°, $C_{20}H_{18}N_4S$ Found C 69.48, H 5.36, N 16.20, S 9.44%;

Requires C 69.34, H 5.24, N 16.17, S 9.26%.

References for starting materials

2-Ethylmercapto-4-hydroxythieno[3,2-d]pyrimidine. GB 1,309,182.

2,4-Dichlorothieno[2,3-d]pyrimidine. GB 1,570,494.

2,4-Dichlorothieno[3,2-d]pyrimidine. GB 1,309,182.

Biological Data.

(A) $H^+ K^+$ ATPase Activity.

The effects of a single high concentratration (100 μM) of a compound of structure (I) on K-stimulated ATPase activity in lyophilised gastric vesicles was determined. Preferred compounds of structure (I) were also tested over a range of concentrations to determine $IC_{50}$ values.

(i) Preparation of lyophilised gastric vesicles (H/K-ATPase).

Lyophilised gastric vesicles were prepared from pig fundic mucosa after the method of Keeling et. al. (Biochem. Pharmacol., 34, 2967, 1985).

(ii) $K^+$-stimulated ATPase activity.

$K^+$-stimulated ATPase activity was determined at 37° C. in the presence of the following : 10 mM Pipes/Tris buffer pH 7.0, 2 mM MgSO$_4$, 1 mM KCl, 2 mM Na2ATP and 3-6 μg protein/ml lyophilised gastric vesicles. After incubation for 30 minutes, the inorganic phosphate hydrolysed from ATP was determined by the method of Yoda and Hokin (Biochem. Biophys. Res. Commun. 40, 880, 1970).

Compounds of structure (I) were dissolved in dimethylsulphoxide which up to the highest concentration used had no effect on $K^+$-stimulated ATPase activity.

The effect of the highest concentration of each compound of structure (I) on the recovery of a standard amount of inorganic phosphate was also determined.

(iii) Results.

The compounds of the example 1 to 6 and 8 had $IC_{50}$ values in the range of from 0.02 to 0.5 μM.

EXAMPLE A

A tablet for oral administration is prepared by combining

| | Mg/Tablet |
|---|---|
| Compound of structure (I) | 100 |
| lactose | 153 |
| Starch | 33 |
| crospovidone | 12 |
| microcrystalline cellulose | 30 |
| magnesium stearate | 2 |

| | Mg/Tablet |
|---|---|
| | 330 mg | into a 9 mm tablet.

EXAMPLE B

An injection for parenteral administration was prepared from the following

| | % w:w |
|---|---|
| Compound of Structure (I) | 0.50% (w:v) |
| 1M citric acid | 30% (v:v) |
| sodium hydroxide (qs) | to pH 3.2 |
| water for injection EP | to 100 ml |

The compound of Structure (I) was dissolved in the citric acid and the pH slowly adjusted to pH 3.2 with the sodium hydroxide solution. The solution was then made up to 100 ml with water, sterilised by filtration and sealed into appropriately sized ampoules and vials.

What is claimed is:

1. A compound of structure (I)

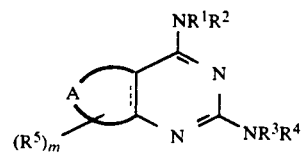

in which $R^1$ is phenyl unsubstituted or substituted by 1 to 3 substituents selected from $C_{1-4}$ alkyl, $C_{1-4}$alkoxy, $C_{1-4}$alkylthio, halogen, cyano, amino, hydroxy, carbamoyl, carboxy, $C_{1-4}$alkanoyl or $CF_3$; and $R^2$ is hydrogen, $C_{1-4}$alkyl, or —(CH$_2$)$_n$Ar in which n is 0 to 4 and Ar is phenyl unsubstituted or substituted by 1 to 3 substituents selected from $C_{1-4}$alkyl, $C_{1-4}$alkoxy, $C_{1-4}$alkylthio, halogen, cyano, amino, hydroxy, carbamoyl, carboxy, $C_{1-4}$alkanoyl or $CF_3$;

$R^3$ is phenyl unsubstituted or substituted by 1 to 3 substituents selected from $C_{1-4}$alkyl, $C_{1-4}$alkoxy, $C_{1-4}$alkylthio, halogen, cyano, amino, hydroxy, carbamoyl, carboxy, $C_{1-4}$alkanoyl or $CF_3$; and $R^4$ is hydrogen, $C_{1-4}$alkyl, or —(CH$_2$)$_n$Ar$^1$ in which n is 0 to 4 and Ar$^1$ is phenyl unsubstituted or substituted by 1 to 3 substituents selected from $C_{1-4}$alkyl, $C_{1-4}$alkoxy, $C_{1-4}$alkylthio, halogen, cyano, amino, hydroxy, carbamoyl, carboxy, $C_{1-4}$alkanoyl or $CF_3$; and $R^5$ is hydrogen, $C_{1-4}$alkyl, $C_{1-4}$alkoxy or COC$_{1-4}$alkyl;

n is 1 or 2;

A is —SCH=CH—, or —CH=CHS—, and the dotted line indicates the presence of a double bond;

or a pharmaceutically acceptable salt thereof.

2. A compound according to claim 1 in which $R^2$ is $C_{1-4}$alkyl.

3. A method of inhibiting gastric acid secretion which comprises administering to a subject in need thereof an effective amount of a compound of formula IA:

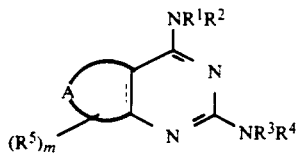

in which
- $R^1$ and $R^2$ are the same, or different and are each hydrogen, $C_{1-4}$alkyl, $-(CH_2)_nAr$ in which n is 0 to 4 and Ar is a phenyl group, unsubstituted or substituted by one to three substituents selected from $C_{1-4}$alkyl, $C_{1-4}$alkoxy, $C_{1-4}$alkylthio, halogen, cyano, amino, hydroxy, carbamoyl, carboxy, $C_{1-4}$alkanoyl or $CF_3$; and
- $R^3$ and $R^4$ are the same, or different and are each hydrogen, $C_{1-4}$alkyl, $-(CH_2)_nAr^1$ in which n is 0 to 4 and $Ar^1$ is a phenyl group, unsubstituted or substituted by one to three substituents selected from $C_{1-4}$alkyl, $C_{1-4}$alkoxy, $C_{1-4}$alkylthio, halogen, cyano, amino, hydroxy, carbamoyl, carboxy, $C_{1-4}$alkanoyl or $CF_3$; and
- $R^5$ is hydrogen, $C_{1-4}$alkyl, $C_{1-4}$alkoxy or $COC_{1-4}$alkyl;
- n is 1 or 2;
- A is $-SCH=CH-$, $-CH=CHS-$, or $=CHSCH=$, and the dotted line indicates the presence of a double bond when A is $-SCH=CH-$ or $-CH=CHS-$;

or a pharmaceutically acceptable salt thereof.

4. A method of inhibiting bone resorption which comprises administering to a subject in need thereof, an effective amount of a compound of claim 1.

5. A compound according to claim 1 which is 2-(2-Methylphenylamino)-4-(N-methylphenylamino)thieno[3,2-d]pyrimidine.

6. A compound according to claim 1 which is 2-(4-Methoxy-2-methylphenylamino)-4-(N-methylphenylamino)thieno[3,2-d]pyrimidine hydrochloride.

7. A compound according to claim 1 which is 2-(4-fluoro-2-methylphenylamino)-4-(N-methylphenylamino)thieno[3,2-d]pyrimidine hydrochloride 8. A compound according to claim 1 which is 2,4-Bis(N-methylphenylamino)thieno[3,2-d]pyrimidine 9. A compound according to claim 1 in which is 2-(2-Methylphenylamino)-4-(N-methylphenylamino)thieno[2,3-d]pyrimidine hydrochloride.

10. A compound according to claim 1 which is 2-(4-Fluoro-2-methylphenylamino-4-(N-methylphenylamino)thieno-[2,3-d]pyrimidine hydrochloride 11. A compound according to claim 1 which is 2-(2-Methylphenylamino)-4-(phenylamino)-thieno[2,3d]-pyrimidine hydrochloride 12. A compound according to claim 1 which is 2,4-Bis-(N-methylphenylamino)thieno(2,3-b)pyrimidine.

13. A compound according to claim 1 which is 2,4-Bis(2-methylphenylamino)thieno)2,3-d)pyrimidine or a pharmaceutically acceptable salt thereof, 14. A pharmaceutical composition comprising a compound according to claim 1 and a pharmaceutical carrier.

* * * * *